US00PP27601P3

(12) United States Plant Patent
Lee

(10) Patent No.: US PP27,601 P3
(45) Date of Patent: Jan. 24, 2017

(54) ***GARDENIA* PLANT NAMED 'LEETWO'**

(50) Latin Name: *Gardenia hybrida*
Varietal Denomination: LEETWO

(71) Applicant: Robert Edward Lee, Independence, LA (US)

(72) Inventor: Robert Edward Lee, Independence, LA (US)

(73) Assignee: PDSI, Loxley, AL (US)

( * ) Notice: Subject to any disclaimer, the term of this patent is extended or adjusted under 35 U.S.C. 154(b) by 171 days.

(21) Appl. No.: 14/121,171

(22) Filed: Aug. 11, 2014

(65) Prior Publication Data

US 2016/0044847 P1 Feb. 11, 2016

(51) Int. Cl.
*A01H 5/02* (2006.01)

(52) U.S. Cl.
USPC ..... Plt./255

(58) Field of Classification Search
USPC ..... Plt./255
See application file for complete search history.

*Primary Examiner* — Keith Robinson
(74) *Attorney, Agent, or Firm* — Cassandra Bright

(57) ABSTRACT

A new and distinct *Gardenia* cultivar named 'LEETWO' is disclosed, characterized by distinctive small, very fragrant white, radial flowers. Plant form is highly compact and dense and suitable for Southern climates. The new cultivar is a *Gardenia*, suitable for ornamental garden purposes.

2 Drawing Sheets

Latin name of the genus and species: *Gardenia hybrida*. Variety denomination: 'LEETWO'.

BACKGROUND OF THE INVENTION

The new cultivar is a product of a planned breeding program by the inventor. This new variety, hereinafter referred to as 'LEETWO', was found as an openly pollinated seedling in a group of *Gardenia jasminoides* 'Daisy' (unpatented) seedling plants being grown in Independence, La. The inventor, Robert Edward Lee, discovered the seedling in Independence, La., at a research nursery during October of 2000.

After identifying the new variety as a potentially interesting selection, the inventor first organized propagation of 'LEETWO' by vegetative cuttings during 2004 at the same commercial nursery in Independence, La. The inventor continued confidential, controlled testing and propagation, assessing stability of the unique characteristics of this variety. Multiple generations have been reproduced and have shown that the unique features of this cultivar are stable and reproduced true to type.

SUMMARY OF THE INVENTION

The cultivar 'LEETWO' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'LEETWO' These characteristics in combination distinguish 'LEETWO' as a new and distinct *Gardenia* cultivar:

1. Unique, dense plant form.
2. Tolerance for heat and disease
3. Adaptability to production and use in Southern climates.

4. Excellent fragrance.
5. Extremely compact growth
6. Deep green, shiny foliage
7. Good specimen plant
8. Good container plant

COMPARISON TO PARENT VARIETY

'LEETWO' is similar in most horticultural characteristics to the seed parent variety *Gardenia* 'Daisy' unpatented. Plants of the new cultivar 'LEETWO' however, produce flowers that are smaller and stronger, than the seed parent variety. Additionally, plant habit is overall more compact in the new variety, than the parent, and foliage is darker green and shinier.

The pollen parent is unknown.

COMMERCIAL COMPARISON

'LEETWO' can be compared to the commercial variety *Gardenia hybrida* 'Leethree', U.S. Plant patent application Ser. No. 14/121,180, filed concurrently. Plants of the new cultivar 'LEETWO' are similar to plants of 'Leethree' in most horticultural characteristics, however, plants of the new cultivar 'LEETWO' produce more branches, forming a denser plant than this comparator.

BRIEF DESCRIPTION OF THE PHOTOGRAPHS

Figure 1:
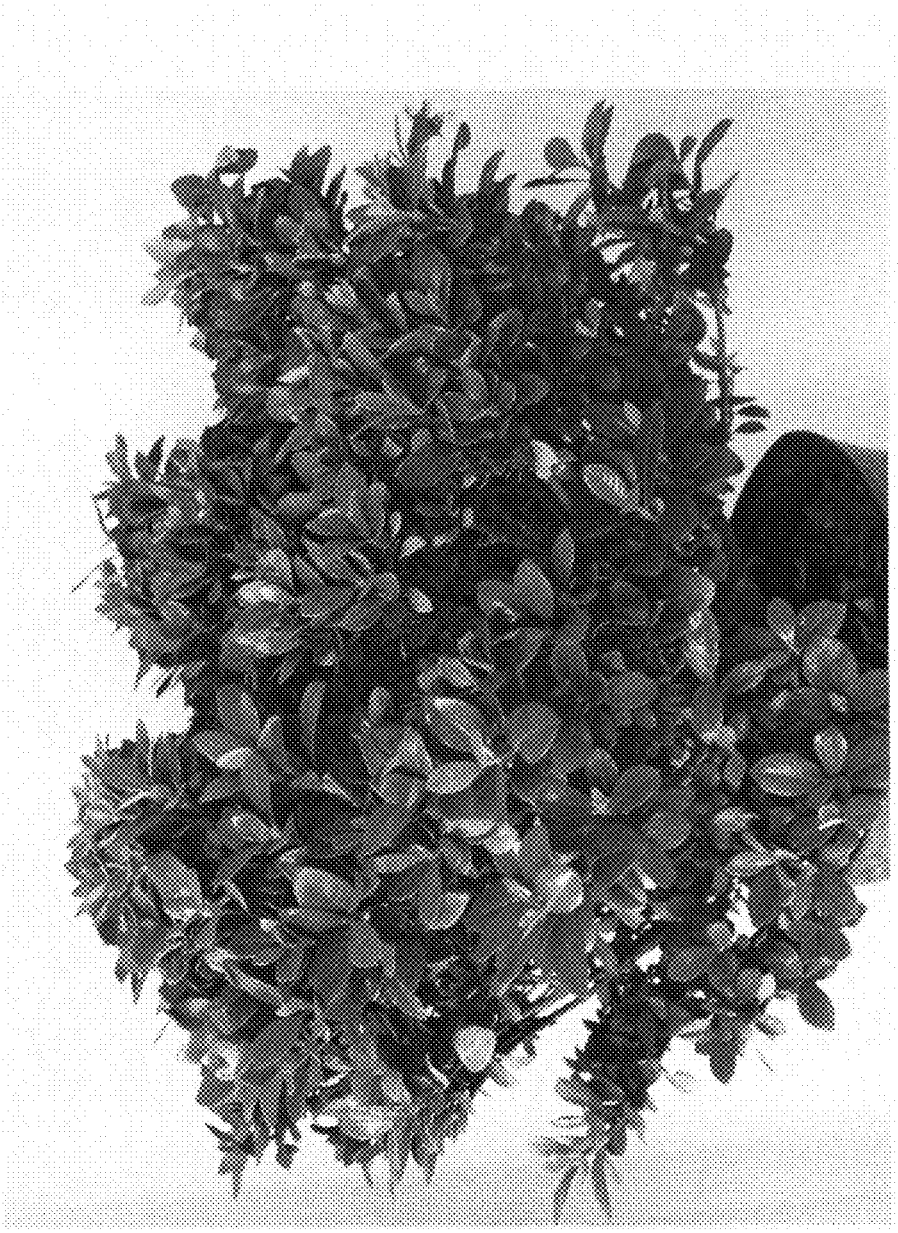

The accompanying photograph in FIG. 1 illustrates in full color a typical plant of the new variety.

Figure 2:
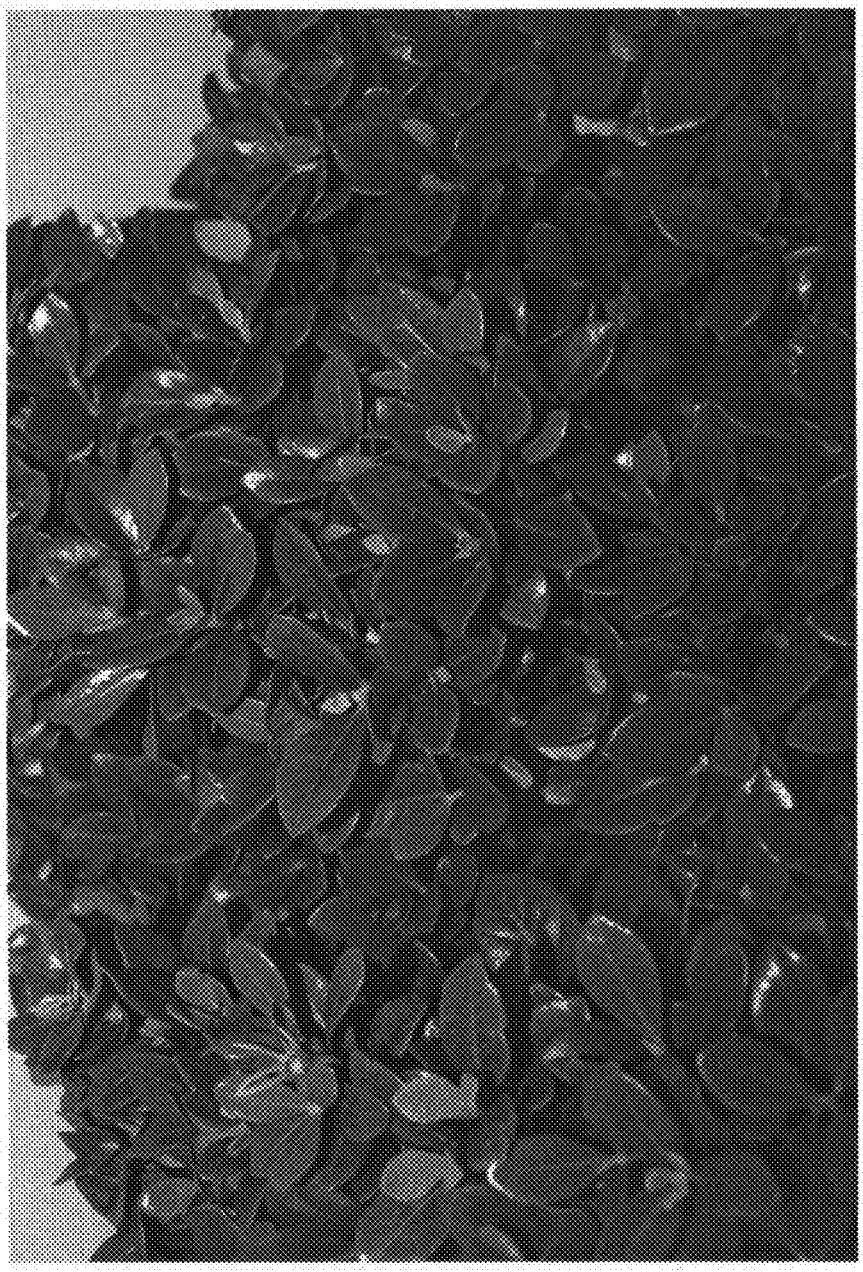

FIG. 2 shows a close up of foliage of 'LEETWO' grown outdoors in Alabama. The plant is approximately 2 years old, and is shown in a three gallon container. The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007 except where general terms of ordinary dictionary significance are used. The following observations and measurements describe 'LEETWO' plants grown outdoors in Loxley, Ala. Plants are approximately 3 years old, in a 3 gallon nursery container. Measurements and numerical values represent averages of typical plant types.

Botanical classification: *Gardenia hybrida* 'LEETWO'.

PROPAGATION

Typically by semi-hardwood cuttings in Spring and Summer.

Root description: Woody to semi-wood. Colored near RHS Brown 200D. Moderately well-branched.

Time to initiate roots: About 4 to 6 weeks in the Summer.

Time to produce a rooted young plant: Approximately 12 weeks in the Summer.

PLANT

Growth habit: Globular shrub.

Height: Approximately 35 cm to top of foliar and flowering plane.

Plant spread: Approximately 50 cm.

Branching characteristics: Well branched, approximately 4 to 6 lateral branches emerge from a pinch. Branches occur at approximately 35° angles.

Primary branches:

- *Length of primary branches.*—Average 12 cm, then pinched and new branches emerge.
- *Diameter of primary branches.*—Approximately 0.7 cm.
- *Primary branch strength.*—Very strong, flexible difficult to break.
- *Primary branch color.*—Mature branches are colored a mottled mixture of Grey 143C, Greyed-Green 189A and Grey-Brown N199A. Young branches near Grey-Brown N199B and Brown 200B. Very small patches of Green 143A.
- *Primary branch texture.*—Mature branches very rough and slightly scaly. Young growth very scaly.

Age of plant described: Approximately 2 years.

Lateral branches:

- *Color.*—Upper section near RHS Yellow-Green 144B, lower section near Grey-Brown 199A.
- *Length.*—Average range 7 to 15 cm.
- *Diameter.*—Approximately 0.4 cm.
- *Aspect.*—Straight, attached at angles from approximately 15 to 30 degrees.
- *Texture.*—Slightly canescent.
- *Strength.*—Strong, flexible.
- *Internode.*—Average range 1.1 cm to 2.8 cm.

FOLIAGE

Leaf:

- *Type.*—Simple.
- *Arrangement.*—Opposite. At end of branches tightly spaced, to appear whorled.
- *Average length.*—Approximately 5.7 cm.
- *Average width.*—Approximately 2.6 cm.
- *Shape of blade.*—Obovate.
- *Apex.*—Acute.
- *Base.*—Broad attenuate.
- *Attachment.*—Sessile.
- *Margin.*—Entire.
- *Texture of top surface.*—Glabrous.
- *Texture of bottom surface.*—Glabrous.
- *Appearance of top surface.*—Very glossy.
- *Appearance of bottom surface.*—Matte.
- *Color.*—Young foliage upper side: Near RHS Yellow-Green 144A, but darker. Young foliage under side: Near RHS Yellow-Green 144B. Mature foliage upper side: Near RHS Green 139A. Mature foliage under side: Near RHS Green 137D.
- *Venation.*—Type: Pinnate. Venation color upper side: Near RHS Yellow-Green N144B Venation color under side: Near RHS Yellow-Green 144B.

FLOWER

Bloom period: Plants flower in the Spring, then begin intermittent flowering cycles in later Spring/Summer through Fall in Southern California.

Inflorescence:

- *Arrangement.*—Single rotate flowers arise from upper leaf axils.

Peduncle:

- *Length.*—Average 0.7 cm.
- *Diameter.*—0.3 cm.
- *Color.*—Near RHS Green 143C.
- *Texture.*—Glabrous.
- *Aspect.*—Straight.
- *Angle.*—Acute.

Flowers:

- *Length.*—Average 3.0 to 4.5 cm.
- *Diameter.*—Average range 4.0 to 4.5 cm.
- *Facing direction.*—Outwardly and upwardly facing.
- *Persistent or self-cleaning.*—Persistent.
- *Fragrance.*—Very strong Tube:

- *Description.*—Tube section of corolla in very tightly held by calyx.
- *Tube length.*—Approximately 1.5 to 2.0 cm.
- *Tube width a widest point.*—Approximately 0.8 cm.
- *Tube width and narrowest point.*—Approximately 0.4 cm.
- *Color.*—Inner: Near RHS White 155C, flushed Green-White 157A Green 143C. Outer: Near RHS White 155C, heavily color with Green 143C.

Petals:

- *Unfused petal segments.*—Length: Approximately 1.2 cm. Width: Approximately 1.6 cm.
- *Arrangement.*—Rotate.
- *Apex.*—Rounded, occasionally acute.
- *Base.*—Fused.
- *Shape of petal.*—Obovate.
- *Petal margin.*—Entire.
- *Petal arrangement.*—Rotate, slightly overlapping, fused approximately ⅓ from base.
- *Petal number.*—7.
- *Petal texture.*—Smooth, all surfaces.

Color:

*Upper surface at first opening*.—Near RHS White 155C.

*Under surface at first opening*.—Near RHS White 155C. Large streak of Yellow-Green N144C over approximately ⅓ of length.

*Inner surface at maturity*.—Near RHS White 155C.

*Outer surface at maturity*.—Irregular, faint streak of Yellow-Green N144C over approximately ¼ to ⅓ of length.

*Upper surface at fading*.—Near RHS Yellow 12D.

*Under surface at fading*.—Near RHS Yellow 13C.

Bud:

*Shape*.—Elliptic.

*Length*.—Average 3.5 cm.

*Diameter*.—1.8 cm.

*Color*.—Near RHS White 155C and Yellow-Green N144C.

Calyx/sepals:

*Quantity per flower*.—5 sepals.

*Shape*.—Narrow deltate, base fused.

*Length*.—Average 2.0 cm.

*Width*.—Sepal 0.2 cm, calyx 1.0 at widest point.

*Apex*.—Acute.

*Base*.—Fused.

*Margin*.—Entire.

*Texture*.—Glabrous all surfaces. Color: Inner Surface: Near RHS Green 143A. Outer surface: Near RHS Green 137A.

REPRODUCTIVE ORGANS

Stamens:

*Number*.—7 or sometimes 6. Androeceium fused to floral tube, except anthers.

*Length*.—1.1 cm, anthers only.

*Width*.—0.1 to 0.2 cm.

*Anthers*.—Anthers reflexed back, and attached to petals. Length: Approximately 0.7 cm. Width: Approximately 1 mm. Color: Near RHS Greyed-Orange 163CB, turning 163A with age. Pollen: None observed.

Pistil:

*Number*.—1.

*Length*.—3.0 cm.

*Style*.—Length: 1.5 cm. Color: Near RHS Green-While 155C.

*Stigma*.—3 lobed globular, colored near Yellow 12B. Occasionally 5 observed.

*Ovary*.—Approximately 0.3 cm in diameter, 0.4 long. Colored near Yellow-Green 1C.

OTHER CHARACTERISTICS

Disease and pest resistance: Observed to be less susceptible to normal diseases and pest of *Gardenia hybrida*. Typical diseases of *Gardenia* include *Erysiphe polygoni*, and *Phomopis gardenia*. Pests include the nematode *Meliodogyne* spp., white fly *Dialeurodes citri* and various scales, including *Ceroplastes japonicas, Icerya purchase, Fiorinia theae, Hemiberlesia rapax* and *Aspidiotus nerii*.

Temperature tolerance: USDA Zone 8.

Fruit/seed production: Not observed to date.

What is claimed is:

1. A new and distinct cultivar of *Gardenia* plant named 'LEETWO' as herein illustrated and described.

* * * * *